United States Patent
den Heijer et al.

[11] Patent Number: 5,807,331
[45] Date of Patent: Sep. 15, 1998

[54] ACTIVE PERFUSION DILATATION CATHETER

[75] Inventors: Peter den Heijer, Haren, Netherlands; Ronald J. Solar, San Diego, Calif.

[73] Assignee: Cordis Corporation, Miami Lakes, Fla.

[21] Appl. No.: 649,962

[22] Filed: Apr. 24, 1996

Related U.S. Application Data

[63] Continuation of Ser. No. 230,385, Apr. 20, 1994, abandoned.

[51] Int. Cl.$^6$ .................................................. A61M 25/00
[52] U.S. Cl. ........................... 604/101; 604/53; 604/151; 604/280; 128/772; 606/194
[58] Field of Search ............................. 604/96–101, 264, 604/280, 22, 28, 43, 53, 131, 151; 128/772, 656–658; 606/192, 194

[56] References Cited

U.S. PATENT DOCUMENTS

| | | | |
|---|---|---|---|
| 4,195,637 | 4/1980 | Gruntzig et al. . | |
| 4,323,071 | 4/1982 | Simpson et al. . | |
| 4,545,390 | 10/1985 | Leary . | |
| 4,581,017 | 4/1986 | Sahota . | |
| 4,610,662 | 9/1986 | Weikl | 604/101 |
| 4,763,654 | 8/1988 | Jang | 604/101 |
| 4,771,777 | 9/1988 | Horzewski et al. . | |
| 4,877,031 | 10/1989 | Conway | 604/96 |
| 4,909,252 | 3/1990 | Goldberger | 606/194 |
| 4,921,483 | 5/1990 | Wijay et al. . | |
| 4,944,745 | 7/1990 | Sogard et al. . | |
| 5,135,484 | 8/1992 | Wright | 604/101 |
| 5,163,905 | 11/1992 | Don Michael | 604/101 |
| 5,304,132 | 4/1994 | Jang | 604/101 |
| 5,312,344 | 5/1994 | Grinfeld | 604/101 |
| 5,320,605 | 6/1994 | Sahota | 604/101 |
| 5,378,229 | 1/1995 | Layer et al. . | |
| 5,403,274 | 4/1995 | Cannon . | |
| 5,415,636 | 5/1995 | Forman . | |
| 5,484,412 | 1/1996 | Pierpont | 604/101 |
| 5,514,092 | 5/1996 | Forman et al. . | |

OTHER PUBLICATIONS

Ebel, et al "New Balloon Catheter for Prolonged Percutaneous Transluminal Coronary Angioplasty and Bypass Flow in Occluded Vessels" Catheterization and Cardiovascular Diagnosis 12:116–123 (1986).

*Primary Examiner*—Corrine M. McDermott
*Assistant Examiner*—Chalin Smith
*Attorney, Agent, or Firm*—Michael W. Montgomery

[57] ABSTRACT

The invention relates to an active perfusion dilatation catheter. More particularly, the invention relates to an active perfusion dilatation catheter comprising a catheter shaft having proximal and distal portions and one or more inflation lumens extending therethrough; an inflatable dilatation balloon positioned external to the distal portion of the catheter shaft and in fluid communication with an inflation lumen; an occlusion balloon positioned external to the distal portion of the catheter shaft and proximal to the dilatation balloon and in fluid communication with an inflation lumen; and a perfusion lumen at the distal portion of the catheter shaft, the perfusion lumen having proximal and distal openings, the proximal opening being located proximal to the occlusion balloon and the distal opening being located distal to the inflation balloon.

16 Claims, 2 Drawing Sheets

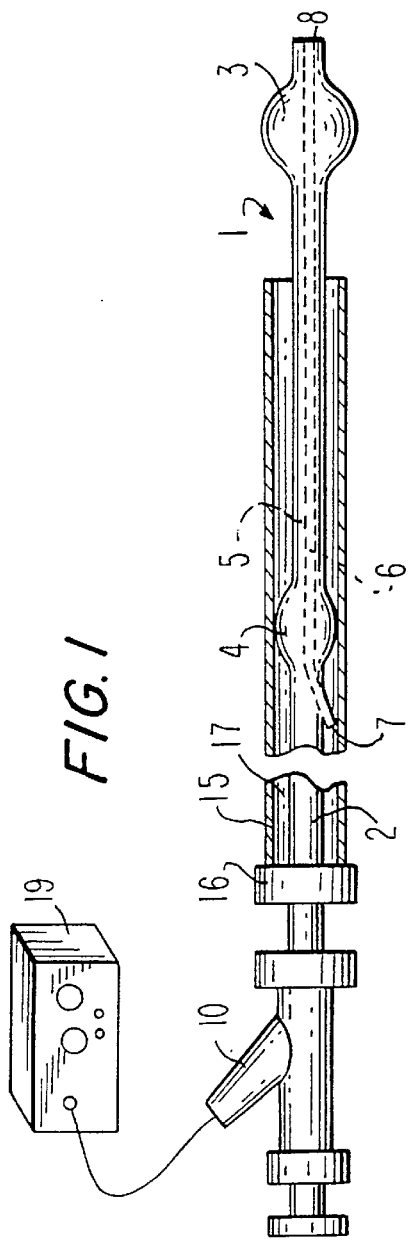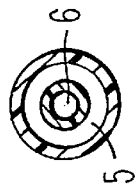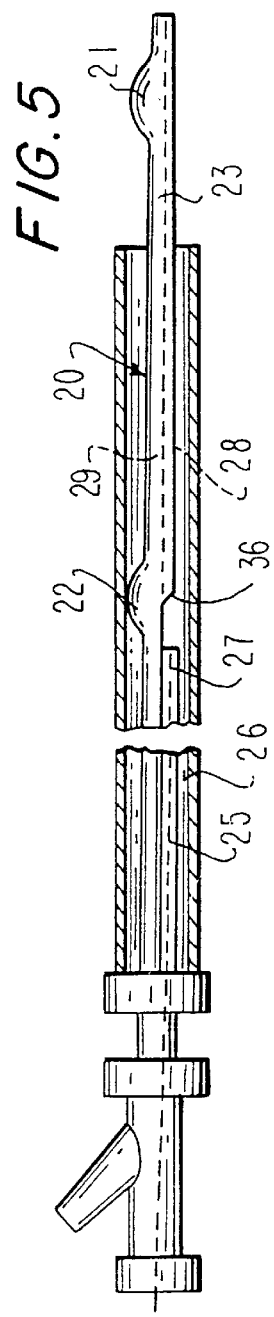

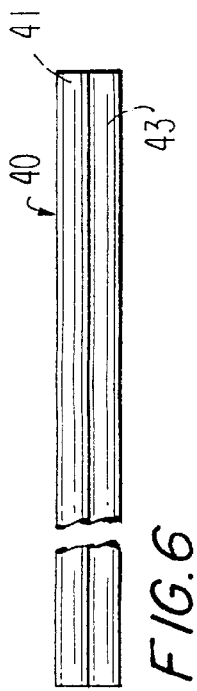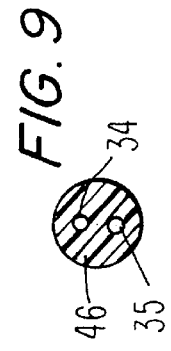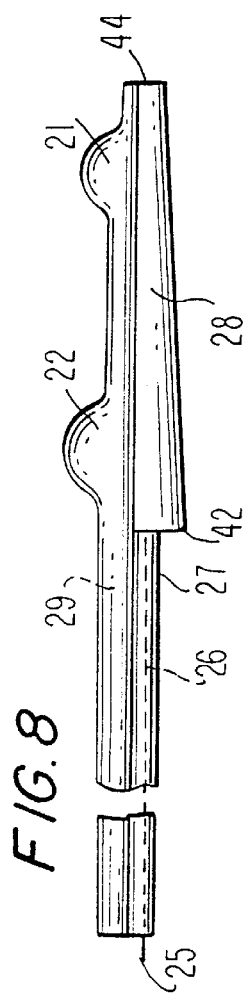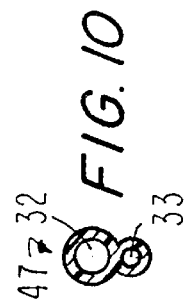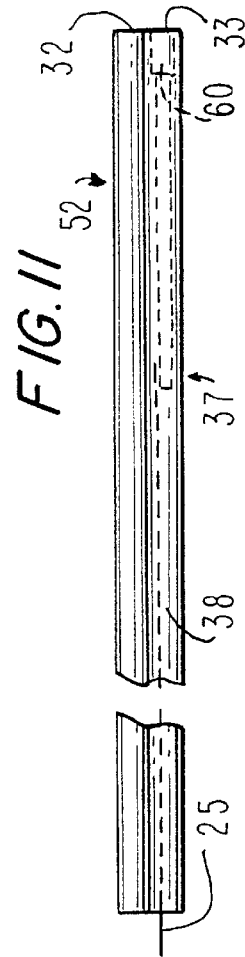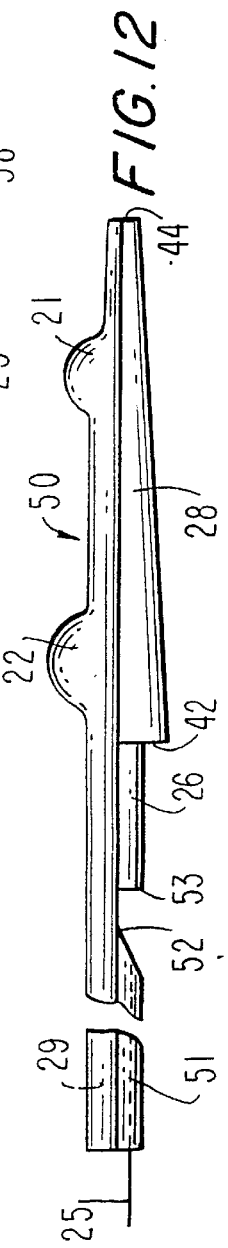

ACTIVE PERFUSION DILATATION CATHETER

This is a continuation of application Ser. No. 08/230,385, filed on Apr. 20, 1994, now abandoned.

FIELD OF THE INVENTION

This invention relates to an active perfusion catheter. More particularly, this invention relates to an active perfusion catheter that utilizes a dilatation balloon to dilate strictures or stenoses within the human body and allows perfusion of blood or other oxygen-bearing fluid distal to the stricture or stenosis during balloon inflation.

BACKGROUND OF THE INVENTION

During percutaneous transluminal coronary angioplasty (PTCA), a narrowed or stenosed coronary artery is enlarged by dilatation with a balloon catheter. When the dilatation balloon is inflated during PTCA, the artery is totally occluded. Prolonged occlusion prevents blood-carrying oxygen, from reaching the heart muscle (myocardium), and may result in myocardial ischemia. Grüntzig et al., U.S. Pat. No. 4,195,637, first discussed using a roller pump to perfuse blood through the lumen of a PTCA catheter to prevent myocardial ischemia during a PTCA procedure. Since then, others have described various ways to perfuse blood or other oxygen-bearing fluids during PTCA, either actively (using an external pump means) or passively (no pump).

For example, Horzewski et al., U.S. Pat. No. 4,771,777, Sogard et al., U.S. Pat. No. 4,944,745, Sahota, U.S. Pat. No. 4,581,017, and Erbel et al., "New Balloon Catheter for Prolonged PTCA and Bypass flow in Occluded Vessels," *Catheterization and Cardiovascular Diagnosis,* 12:116–123 (1986), each describe passive perfusion PTCA catheters. Since these are passive perfusion devices, each relies on the arterial blood pressure of the patient to supply the driving force to push the blood through the catheter. Each patient's blood pressure may vary, and as is often the case, this pressure may be insufficient to provide adequate perfusion to prevent ischemic complications.

Active perfusion PTCA catheter systems, such as described by Grüntzig et al., as above, and Wijay, et al., U.S. Pat. No. 4,921,483, use various pump or plunger means to pump blood or other fluid through the lumen of a PTCA catheter. However, due to the small diameter and long length required for PTCA catheters, high driving pressures are necessary to pump the blood through the lumen of the catheter. This may result in high shear stress and hemolysis of the blood cells.

Thus, there is a need for an active perfusion balloon PTCA catheter which would operate at lower driving pressure.

OBJECTS OF THE INVENTION

It is an object of the invention to provide an active perfusion dilatation catheter.

It is also an object of the invention to provide an active perfusion dilatation catheter wherein a dilatation balloon dilates strictures or stenoses within the human body and blood or other oxygen-bearing fluid is perfused distal to the stricture or stenosis during balloon inflation.

It is a further object of the invention to provide an active perfusion dilatation catheter where the pressure necessary to pump the blood or other oxygen-bearing fluid through the catheter is reduced as compared to known active perfusion dilatation catheters.

It is a yet further object of the invention to provide an active perfusion dilatation balloon catheter wherein the length of the blood perfusion lumen of the catheter is less than that of the dilatation balloon inflation lumen.

It is also an object of the invention to provide a balloon dilatation perfusion catheter that has a lumen positioned exterior to the balloon.

It is an additional object of the invention to provide an active perfusion balloon dilatation catheter that is easy to manufacture.

These and other objects of the invention will become more apparent from the discussion below.

BRIEF DESCRIPTION OF THE DRAWINGS

FIG. 1 is a perspective, partly cross-sectional view of an embodiment of the catheter of the invention;

FIGS. 2 to 4 are each a cross-sectional view of the catheter shown in FIG. 1;

FIG. 5 is a perspective, partly cross-sectional view of another embodiment of the catheter system of the invention;

FIGS. 6, 8, and 11 represent perspective views of a distal portion of a catheter of the invention as it is being formed;

FIGS. 7, 9, and 10 represent cross-sectional views of workpieces from which a catheter of the invention can be formed; and FIG. 12 is a prespective, partly cross-sectional view of a further embodiment of the catheter of the invention.

DESCRIPTION OF THE INVENTION

According to the invention, a balloon dilatation catheter is capable of active perfusion when the dilatation balloon is inflated. The primary distinguishing feature of the catheter of the invention is that, unlike other known active perfusion catheters, there is a second balloon proximal to the dilatation balloon. The catheter has a main shaft, containing a first lumen which is used to inflate the balloons, and a second lumen used for the perfusion of blood, the length of the second lumen being substantially less than that of the first lumen. The distal balloon dilates blood vessel strictures or stenoses, and the proximal balloon serves to occlude the annular space formed between the guiding catheter and the main shaft. A hub means at the proximal end of the catheter is in fluid communication with the inflation lumen and allows connection to an inflation device. The perfusion lumen is open at both its proximal and distal ends, and the proximal end of the perfusion lumen is positioned proximal to the proximal, occlusion balloon while its distal end is distal to the distal dilatation balloon.

In known active perfusion catheters a blood pump is connected to the proximal end of the perfusion lumen. The pressure required to pump the blood through the lumen is proportional directly to length of the lumen and inversely to the fourth power of the lumen diameter. Since PTCA catheters must be long and have a very small diameter to be used clinically, the pressure required to pump blood through the catheter lumen, at a flow rate that will prevent ischemic complications, is significantly high. Such high pressures may result in hemolysis and lead to thrombotic complications.

In this invention, blood is pumped through the guiding catheter. When the occlusion balloon of the invention is inflated, the distal segment of the guiding catheter is occluded, and the blood is directed through the shorter perfusion lumen. Since the lumen of the guiding catheter is much larger than that of the perfusion lumen, and since the distance the blood must travel through the smaller diameter perfusion lumen is relatively short, the pressure required to pump the blood is greatly reduced, as compared to the pressure required to pump blood through a perfusion lumen that extended to the proximal end of the guiding catheter.

The invention can perhaps be better appreciated by making reference to the drawings. In FIG. 1, an active perfusion balloon catheter 1 comprises a main catheter shaft 2 having dilatation balloon 3 and occlusion balloon 4. Catheter shaft 2 contains balloon inflation lumen 5. The distal portion of shaft 2 also contains perfusion lumen 6, where the proximal opening 7 of lumen 6 is proximal to occlusion balloon 4 and the distal opening 8 of lumen 6 is distal to dilatation balloon 3. A Y-connecter 10 is positioned at the proximal end of guiding catheter 15.

In use, the active perfusion dilatation catheter is introduced through a guiding catheter 15. The proximal end 16 of the guiding catheter 15 is sealingly connected to Y-connecter 10. Blood or other oxygen-bearing fluid from a perfusion pump 19 is introduced through the Y-connecter 10 into the annular space 17 between the shaft 2 and the guiding catheter 15. The blood or other fluid travels distally to point proximal to occlusion balloon 4 where it enters the proximal opening 7 of perfusion lumen 6 and travels distally to distal opening 8.

The structure of the shaft 2 where it encompasses lumens 5 and 6 can vary. FIGS. 2 to 4 are each a cross-sectional representation across the distal portion of shaft 2 between balloons 3 and 4. As shown in FIGS. 2 and 3, lumens 5 and 6 can be adjacent in the axial direction. Alternatively, lumen 5 could be concentric to lumen 6, as shown in FIG. 4.

In the embodiment of the invention shown in FIG. 1, the balloons 3 and 4 are concentric to the shaft 2. According to another, preferred embodiment of the invention, shown in FIG. 5, the dilatation balloon 21 and the occlusion balloon 22 are eccentric to shaft 23. Such a configuration is described in more detail in co-pending, commonly assigned U.S. patent applications Ser. No. 07/969,887, filed Oct. 30, 1992, for RAPID EXCHANGE CATHETER, Ser. No. 08/087,428, filed Jul. 2, 1993, for RAPID WITHDRAWAL CATHETER, Ser. No. 07/969,946, filed Oct. 30, 1992, for PREPARATION OF RAPID EXCHANGE CATHETER, and Ser. No. 08/111,304, filed Aug. 24, 1993, for DILATATION CATHETER WITH ECCENTRIC BALLOON, all of which are incorporated herein by reference. It is within the scope of the invention that one of balloons 21 and 22 could be concentric to catheter shaft 23 and the other one could be eccentric.

The eccentric arrangement shown in FIG. 5 has certain advantages as compared to the concentric balloon arrangement shown in FIG. 1. The primary advantages are ease of manufacture, lower manufacturing costs, higher reliability, i.e., fewer parts and bonds, facilitated stenosis crossing—no balloon bunching, and facilitated angioplasty mechanism—focused force.

It should be further appreciated that the perfusion catheter such as is shown in FIG. 5 can also contain structure for a pushing wire or a guidewire or it may be adaptable for use in the monorail technique when the distal portion of the catheter would be advanced over a guidewire. A pushing wire 25 is shown in FIG. 5 in an optional lumen 26 that has been sealed at the distal portion 27 of pushing wire 25 to grasp said distal portion 27. Alternatively, if portion 26 were not sealed, the catheter 20 could be advanced along a guidewire (not shown) that would extend through lumens 28 and 26. Also, as mentioned above, the catheter 20 could be advanced distally along a guidewire (not shown) extending only through lumen 28.

In an additional alternative embodiment, the portion of lumen 29 proximal to balloon 22 could comprise a hypotube, either within the lumen 29 or in place of lumen 29. The stiffness imparted by such a hypotube would make it unnecessary to have a pushing wire, especially if monorail-type use over a guidewire were envisioned.

Other structural variations are within the scope of the invention. For example, there could be a separate lumen extending the entire length of catheter 1 or 20 for a guidewire, or each of dilatation balloon 3 or 21 and occlusion balloon 4 or 22 could have a separate inflation lumen.

The walls for lumens 5, 6, 28, and 29 can each have a thickness of from about 0.3 to 20 mil., preferably from about 0.5 to 10 mil. The wall for lumen 6 or 28 will most likely be slightly thicker than wall for lumen 5 or 29, respectively.

The lumen walls are comprised of materials conventional to balloon dilatation catheters. Suitable materials include polyolefins such as polyethylene, polyethylene terepthalate, polyurethanes, polyesters, and various copolymers thereof. Pushing wire 25 can be made from any rigid, medically acceptable materials suitable for such use, including, but not limited to wires or hypotubes comprised of stainless steel or other rigid materials.

The construction according to the invention leads to flexibility in product design. For example, the choice of a pushing wire allows the designer to impart various features to the catheter in the form of various flexibility and pushability combinations. Also, a hollow pushing wire, or deletion or removal of the pushing wire, would facilitate infusion of fluids, drugs and/or contrast media through the catheter into the distal vasculature. Further, it is within the scope of the invention that catheter 1 or 20 may have at least one additional, coextensive lumen that would similarly facilitate infusion of additional liquids, drugs and/or contrast media.

The catheter 1 or 20 may have visual length markings along its shaft that would enable the operator to predict when the catheter would exit the guiding catheter into the vasculature. This would reduce the fluoroscopy time. The preferred design would put the markings directly on the pushing wire 25 (heat shrink tubing rings, inks, paints, etc.). Since the pushing wire 25 is encapsulated within the second lumen 26, the markings would not be exposed to the patient (i.e., markings would not come off, and materials which could be toxic if exposed may be used).

The perfusion catheter 1 of the invention wherein the balloons are concentric to the catheter shaft 2 can be prepared according to methods well known to those skilled in the art. Exemplary procedures are provided in Grüntzig et al., U.S. Pat. No. 4,195,637, Simpson et al., U.S. Pat. No. 4,323,071, and Leary, U.S. Pat. No. 4,545,390, each of which is incorporated herein by reference.

The preparation of a catheter 20 according to the invention is shown in FIGS. 6 to 11. After a double lumen workpiece 40 is prepared, the distal end of the workpiece is sealingly clamped, and heat and inflation pressure are applied to cause the distal portion of lumen 41 to expand to form the walls of balloons 21 and 22 and the distal portion of lumen 43 to expand to form lumen 28. The location where heat is applied can be varied to vary the respective lengths of balloons 21 and 22 and lumen 28. Heat sealing or application of suitable adhesive seals the distal portion of ballon 21. Opening 42 is cut into lumen 28, and opening 44 is maintained or created by trimming the distal portion of the catheter. Pushing wire 25 is then inserted into lumen 26, wherein either the remaining distal portion, or more, of lumen 26 is heat shrunk to cause pushing wire 25 to be positively engaged by lumen 26. Alternatively, the distal portion of pushing wire 25 could be affixed by suitable means, such as an adhesive or a plug, in lumen 26.

Workpiece 40 can be prepared by methods well-known to those skilled in the art. In a preferred method workpiece 40 can be prepared by blowing extruded tubing 51, a cross-section of which is shown in FIG. 9.

In a preferred embodiment of the invention, catheter 20 can be prepared from extruded tubing 51 by blowing said tubing 51 under pressure and heating conditions sufficient to produce a catheter piece 52, a cross-section of which is shown in FIG. 10, wherein the diameters of lumens 32 and 33 correspond substantially to the final diameters of balloon 21 and 22 and lumen 28, respectively. The holes or openings 34 and 35 in tubing 51 are not necessarily the same, such that the diameters of lumens 32 and 33 may also differ.

After an opening 37 (corresponding to opening 36) is cut into lumen 33 at a point to define the length of the perfusion lumen 28, a pushing wire 25 is inserted into lumen 38. Pushing wire 25 extends the length of lumen 38 to a point slightly distal of opening 37. Optionally a lubricious liner and/or a reinforcing coil or tube 60 is inserted into the distal end of lumen 33. Then, the distal end of lumen 32 is sealed, and, while lumen 32 is pressurized, heat is applied to the distal portion of catheter piece 52 to cause lumen 33 to slightly shrink around liner or tube 60, which fixedly engages the distal end of pushing wire 25. Next, the portions of catheter piece 52 proximal to balloon 22 and between balloons 21 and 22, are heated to shrink lumen 32 to form the balloons and to shrink lumen 38 around pushing wire 25. The balloon lengths are determined by the exact locations where heat is applied to lumen 32.

In an optional embodiment of the invention shown in FIG. 12, lumen 26 of catheter 50 does not contain a pushing wire but is available in conjunction with lumen 28 to form a passageway for a guidewire (not shown), for example, so that the catheter of the invention could be exchanged rapidly, using a standard length guidewire. Lumen 26 here is shortened as compared to a similar lumen in FIG. 8. The total length of lumen 26 plus lumen 28 in an embodiment of FIG. 12 would be about 20–30 cm versus a total length of about 120–150 cm for lumen 29. An additional lumen 51 extending from the proximal end of the catheter 50 to a point 52 proximal to the proximal end 53 of lumen 26 can optionally contain a pushing wire 25 affixed by glue or other adhesive or by the heat shrinking of lumen 51. The pushing wire 25 is particularly useful to impart stiffness if catheter 50 is exchanged across a guidewire (not shown). Alternatively, if lumen 29 proximal to balloon 22 contains or is replaced by a hypotube, lumen 51 and pushing wire 25 may not be required.

When portions of the catheter are heated, the heating can be effected by a point source of heat, where the point source is moved along the exterior of the catheter or the catheter is moved across the point source. Alternatively, the heat can be applied with a broader heat source, such as a hot water bath. The source of and/or techniques of heating will be apparent to those skilled in the art.

Also, in a preferred embodiment of the invention the workpiece will optionally be cross-linked prior to working. Such cross-linking could be effected by chemical or irradiation means. The workpiece can be optionally or additionally oriented by mechanical means, such as a stretching during blowing.

The catheters of the invention are prepared by use of techniques and procedures known to those skilled in the art. For example, the pressure and heating conditions will vary according to the materials used and the results desired, and it is well within the skill of those skilled in the art to determine the proper pressure and heating requirements.

An additional advantage of the design and preparation according to the invention is that the catheter can be of integral design and multiple bonding steps can be avoided. The balloon and both lumens can be formed from a single piece. This design permits improvements in manufacturing yields, quality, and reliability due to simplified construction.

A guidewire used herein may be a conventional guidewire, preferably a spring guidewire, as is well know. Typical guidewires are shown in U.S. Pat. Nos. 4,757,827, 4,815,478, 4,813,434, 4,619,274, 4,554,929, 4,545,390, 4,538,622, 3,906,938, 3,973,556, and 4,719,924, all of which are incorporated herein by reference. In addition, the shaft of a guidewire could be solid or hollow, such as a hypotube, with an open distal end, to facilitate drug infusion.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An active perfusion dilatation catheter system for dilating a site within a patient's vascular system while actively perfusing a perfusion fluid from outside the patient's body to a location distal from said site, comprising:

a dilatation catheter with a catheter shaft having proximal and distal portions and at least one inflation lumen extending longitudinally therethrough; an inflatable dilatation balloon positioned external to the distal portion of the catheter shaft and in fluid communication with an inflation lumen; an occlusion balloon positioned external to the distal portion of the catheter shaft and proximal to the dilatation balloon and in fluid communication with an inflation lumen; and a perfusion lumen at the distal portion of the catheter shaft, the perfusion lumen communicating between proximal and distal openings defined by said catheter shaft, the proximal opening located proximal to the occlusion balloon, and the distal opening located distal to the dilatation balloon;

a guiding catheter having proximal and distal ends and defining a guiding catheter lumen, said occlusion balloon and a portion of the dilatation catheter shaft being within said guiding catheter lumen, and said dilatation balloon being distal from the guiding catheter distal end, wherein said occlusion balloon occludes said guiding catheter lumen in an inflated state, and said proximal opening communicates with said guiding catheter lumen; and a pump coupled with the guiding catheter proximal end, for pumping said perfusion fluid through said guiding catheter lumen from the guiding catheter proximal end toward the guiding catheter distal end, thereby causing the perfusion fluid to flow into and through said perfusion lumen.

2. The catheter system of claim 1, wherein the dilatation and occlusion balloons are eccentric to the catheter shaft.

3. The catheter system of claim 1, wherein the dilatation and occlusion balloons are concentric to the catheter shaft.

4. The catheter system of claim 1, wherein said catheter shaft defines only one inflation lumen in fluid communication with the dilatation balloon and the occlusion balloon.

5. The catheter system of claim 1, wherein the dilatation and occlusion balloons are each in fluid communication with a separate inflation lumen defined by the catheter shaft.

6. The catheter system of claim 1, wherein said dilatation catheter shaft further comprises a pushing wire.

7. The catheter system of claim 1, wherein said dilatation catheter shaft defines a guidewire lumen proximal to and in fluid communication with the perfusion lumen such that said guidewire lumen and perfusion lumens form a passageway for a guidewire.

8. The catheter system of claim 7, wherein said dilatation catheter shaft defines a pushing lumen extending from the proximal portion of the catheter to a point proximal to the proximal end of said guidewire lumen, and said pushing lumen contains a pushing wire.

9. The active perfusion dilatation catheter system of claim 1, further comprising a guidewire passing through a guidewire lumen defined by said dilatation catheter.

10. The catheter system of Claim 1, wherein said occlusion balloon is formed of an elastic material.

11. The catheter system of claim 1, wherein said dilatation balloon is formed of a substantially inelastic material.

12. A perfusion dilatation catheter system for dilating a site within a patient's vascular system while perfusing a perfusion fluid to a location distal from said site, comprising:

a dilatation catheter having a dilatation catheter shaft, a dilatation balloon disposed near a distal end of the dilatation catheter shaft, an occlusion balloon spaced proximal from the dilatation balloon, and a distal perfusion lumen providing fluid communication between a proximal opening located proximal to the occlusion balloon and a distal opening located distal to the dilatation balloon; and a guiding catheter defining a guiding catheter lumen, said dilatation catheter extending through said guiding catheter lumen such that said occlusion balloon is disposed within said guiding catheter lumen and said dilatation balloon being distal of the guiding catheter distal end, wherein said occlusion balloon occludes said guiding catheter lumen in an inflated state, a proximal perfusion lumen being defined by an annular space between an inner surface of said guiding catheter lumen and an outer surface a proximal portion of said dilatation catheter shaft, and said catheter system provides fluid communication for said perfusion fluid to flow from said proximal perfusion lumen through said distal perfusion lumen to a location distal from said distal opening.

13. The catheter system of claim 12, further comprising a pump coupled with the guiding catheter proximal end adapted to pump the perfusion fluid through said annular space, said occlusion balloon causing the perfusion fluid to enter and flow through the perfusion lumen, said annular space defining a greater flow area than said perfusion lumen.

14. An active perfusion dilatation catheter system comprising;

a guiding catheter defining a guiding catheter lumen; and a dilatation catheter with a catheter shaft having proximal and distal portions;

an inflatable dilatation balloon positioned external to the distal portion of the catheter shaft;

an occlusion balloon positioned external to the distal portion of the catheter shaft and proximal to the dilatation balloon;

a proximal perfusion lumen defined by an annular space between an inner surface of said guiding catheter lumen and an outer surface of said proximal portion of said dilatation catheter shaft; and a distal perfusion lumen at the distal portion of the catheter shaft, the distal perfusion lumen having proximal and distal openings, the proximal opening being located proximal to the occlusion balloon, and the distal opening being located distal to the dilatation balloon, wherein the dilatation balloon remains outside said guiding catheter during dilatation, and said occlusion balloon occludes the guiding catheter lumen when inflated, such that said catheter system provides fluid communication from said proximal perfusion lumen to said distal perfusion lumen.

15. In a method of perfusing blood or another oxygen-containing fluid during a ballon angioplasty procedure wherein a guiding catheter is introduced into a human body, a ballon dilatation catheter is then introduced through the guiding catheter, the dilatation balloon is positioned within a stetonic segment, and the dilatation ballon is inflated, the improvement wherein the balloon dilatation catheter contains an occlusion balloon located proximal to the dilatation balloon, a perfusion lumen extending from a point proximal to the occlusion balloon to a point distal to the dilatation balloon; the positioning occlusion balloon within the guiding catheter inflating the occlusion balloon prior to or simultaneously with inflation of the dilatation balloon, and actively causing blood or other oxygen-bearing fluid to flow distally through the annular space between the guiding catheter and the main shaft of the lumen and the through the perfusion lumen.

16. A method of perfusing blood or another oxygen-containing fluid during a balloon dilatation procedure, comprising the steps of:

introducing a guiding catheter defining a lumen into a blood vessel of a human body;

inserting a balloon dilatation catheter through the guiding catheter;

advancing said dilatation catheter through a guiding lumen defined by the guiding catheter until said dilatation balloon is positioned within a desired site and said occlusion balloon is positioned within the guiding catheter lumen;

inflating said dilatation balloon to expand the desired site and inflating the occlusion balloon to occlude the guiding catheter lumen;

perfusing the oxygen-containing fluid through an annular space formed between said dilatation catheter and the guiding catheter lumen, and then through said perfusion lumen from a point proximal to the occlusion balloon to a point distal to the dilatation balloon.

* * * * *

UNITED STATES PATENT AND TRADEMARK OFFICE
CERTIFICATE OF CORRECTION

PATENT NO : 5,807,331
DATED : September 15, 1998
INVENTOR(S) : den Heijer, et al.

It is certified that error appears in the above-identified patent and that said Letters Patent is hereby corrected as shown below:

Claim 15, Column 8, Line 32 to the dilatation balloon, the positioning occlusion should read to the dilatation balloon, positioning the occlusion Signed and Sealed this Second Day of May, 2000

Attest:

Attesting Officer

Q. TODD DICKINSON

Director of Patents and Trademarks